United States Patent [19]

Watanabe et al.

[11] Patent Number: 4,762,823
[45] Date of Patent: Aug. 9, 1988

[54] NUCLEOSIDES OF 5-MONOFLUOROMETHYLURACIL AND 5-DIFLUOROMETHYLURACIL

[75] Inventors: Kyoichi A. Watanabe, Rye Brook; Jasenka Matulic-Adamic, Mamaroneck; Richard W. Price, Scarsdale; Jack J. Fox, White Plains, all of N.Y.

[73] Assignee: Sloan-Kettering Institute for Cancer Research, New York, N.Y.

[21] Appl. No.: 787,973

[22] Filed: Oct. 16, 1985

[51] Int. Cl.$^4$ .................... A61K 31/70; C07H 19/06
[52] U.S. Cl. ........................................ 514/50; 536/23
[58] Field of Search ................... 536/23; 514/50, 51

[56] References Cited

U.S. PATENT DOCUMENTS

| | | | |
|---|---|---|---|
| 3,870,700 | 3/1975 | Kotick et al. | 536/23 |
| 4,140,850 | 2/1979 | Wierenga | 536/23 |
| 4,210,638 | 7/1980 | Greer | 536/23 |
| 4,334,059 | 6/1982 | Ogilvie | 536/23 |
| 4,382,925 | 5/1983 | deClercq et al. | 536/23 |
| 4,594,339 | 6/1986 | Lopez et al. | 514/50 |

*Primary Examiner*—J. R. Brown
*Assistant Examiner*—Jenny Tou
*Attorney, Agent, or Firm*—John P. White

[57] ABSTRACT

A method for synthesizing monofluoromethyl- and difluoromethyluracil nucleosides from the corresponding thymine nucleosides is developed. These compounds which contain a partially fluorinated methyl group at the C-5 position (a new class of nucleosides) are potential antiviral and/or anticancer agents. The major features of the preparative route involve bromination of suitably protected thymine nucleosides followed by fluoride treatment.

10 Claims, No Drawings

NUCLEOSIDES OF 5-MONOFLUOROMETHYLURACIL AND 5-DIFLUOROMETHYLURACIL

The invention described herein was made in the course of work under Grant No. 18601 from the U.S. Department of Health and Human Services. The U.S. Government has certain rights in this invention.

BACKGROUND

5-Trifluoromethyluracil was originally synthesized in very low yield by a multistep procedure starting from trifluoroacetone cyanohydrin (Heidelberger, et al., J. Am. Chem. Soc., 84, 3597 (1962); J. Med. Chem., 7, 1 (1964)). Later, this compound was prepared more conveniently from uracil-5-carboxylic acid by treatment with sulfur tetrafluoride (Mertes, et al., J. Med. Chem., 9, 876 (1964)). The 2'-deoxynucleoside, i.e., 1-(2'-deoxy-$\beta$-D-erythropentofuranosyl)-5-trifluoromethyluracil or $F_3TDR$, was prepared by condensation of the base and sugar halide in very low yield. (Heidelberger, et al., loc. cit). The trifluoromethyluracil nucleoside has shown activity against herpes simplex and many tumor systems (Heidelberger, Progr. Nucleic Acid Res. Mol. Biol., 4, 1 (1965); Cancer Res., 30, 1549 (1970)).

5-Difluoromethyluracil was also prepared but was found to be extremely labile in neutral aqueous media (Mertes, et al., loc. cit). No nucleoside containing this base has been synthesized. Attempts to synthesize 5-monofluorouracil have failed (Mertes, loc. cit). No 5-monofluoromethyluracil nucleoside is known.

Our theoretical considerations suggest that substitution of the N-1 position of 5-(partially-fluorinated)-methyluracils with an alkyl or sugar moiety should decrease the lability of the fluorine in the heterocyclic base. Therefore, nucleosides containing 5-(partially fluorinated) methyluracils should be obtainable by synthesis from a preformed nucleoside.

SUMMARY

Nucleosides of the invention can be represented by Formula I as follows:

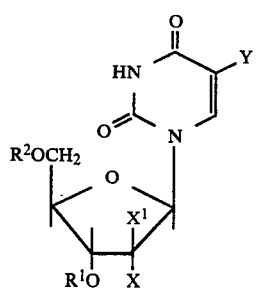

Formula I

Wherein either X or X' is always H and the other is H, $OR^3$, or a halogen such as fluorine, chlorine, bromine or iodine as well as pseudohalogen such as lower alkylsulfonyl group of 1 to 5 carbon atoms such as methyl-, ethyl- propyl-. isopropyl-, butyl-, isobutyl-, sec-butyl-, tert-butyl, and pentylsulfonyl or arylsulfonyl such as benzene-, p-toluene-, p-nitrobenzenesulfonyl grouping.

Y is monofluoromethyl ($CH_2F$) or difluoromethyl ($CHF_2$). $R^1$, $R^2$ and $R^3$ are the same or different and are hydrogen or acyl groups of 1 to 20 carbon atoms such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, arachidonyl and the like, or trisubstituted silyl groups such as tert-butyl-dimethylsilyl, tert-butyldiphenylsilyl, dimethylphenylsilyl and the like.

DESCRIPTION OF INVENTION

The present invention relates to the novel class of nucleosides which contain 5-monofluoromethyluracil or 5-difluoromethyluracil as their aglycon. A further aspect of the present invention relates to processes for preparing uracil nucleosides containing a partially fluorinated methyl group at the C-5 position and intermediates useful therein.

The starting materials for the process of the present invention can be subsumed under general Formula II, as follows:

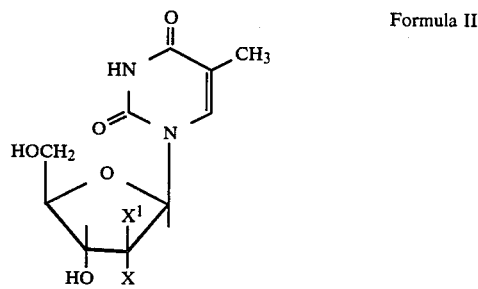

Formula II

X or $X^1$ is as defined previously.

Nucleosides of Formula II are acylated with alkanoic acid chloride or alkanoic acid anhydride in organic base such as pyridine or triethylamine. Acylation of Formula II nucleosides is also achieved with alkanoic acid chloride or alkanoic acid anhydride in aprotic solvent such as methylene chloride, chloroform, dichloroethane or tetrachloroethane in the presence of organic base such as pyridine, lutidine, collidine, triethylamine, N,N-diethylaniline, p-(dimethylamine)pyridine, 1,8-diazabicyclo[5,4,0]undec-7-one or 1,5-diazabicyclo[4,3,0]non-5-ene.

Upon completion of the reaction, the reaction mixture is quenched suitably, by adding excess alkanol such as methanol, ethanol, propanol and the like, to hydrolyze the acylating reagent. After concentration of the mixture, the acylated intermediates can be obtained in pure condition either by direct crystallization of the residue from various solvents or solvent systems, or by chromatography over a column of silica gel G60 using various solvent systems. The acylated intermediates

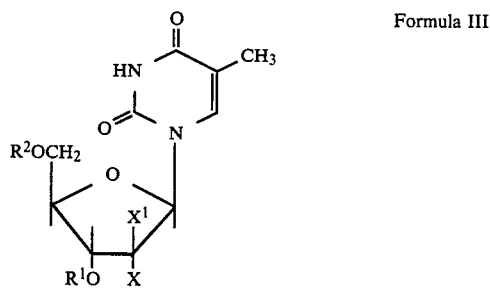

Formula III obtained by the above procedure can be presented under general Formula III, wherein X or $X^1$ is always hydrogen and the other is OR$^3$, or a halogen such as fluorine, chlorine, bromine or iodine as well as pseudohalogen such as pseudohalogen such as lower alkylsulfonyl group of 1 to 5 carbons such as methyl-, ethyl-, propyl-, isopropyl-, butyl-, isobutyl-, sec-butyl-, tert-butyl- and pentylsulfonyl or arylsulfonyl such as benzene-, p-toluene-, p-nitrobenzenesulfonyl grouping.

R$^1$, R$^2$ and R$^3$ are the same and are acyl groups of 1 to 20 carbon atoms such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, arachidonyl and the like.

Nucleosides of Formula II are also converted into the corresponding partially silylated intermediates by treatment with trisubstituted-silyl chloride such as tert-butyldimethylsilyl, tert-butyldiphenylsilyl or dimethylphenylsilyl chloride in organic base such as pyridine or triethylamine. Silylation of Formula II nucleosides can also be performed with trisubstituted-silyl chloride in aprotic solvent such as methylene chloride, chloroform, dichloroethane, tetrahydrofuran, dioxan, benzene, acetonitrile, ethyl acetate and the like in the presence of organic base such as pyridine, lutidine, collidine, triethylamine, N,N-diethylaniline, p-(dimethylamino)pyridine, 1,8-diazabicyclo[5,4,0]undec-7-ene or 1,5-diazabicyclo[4,3,0]non-5-ene. The silylation reaction is carried out at −40° to 147° C. (preferably from 20° to 30° C.), in a period of from 1 hour to 6 days.

When the reaction is carried out without solvent, or in a water-miscible aprotic solvent, the mixture is concentrated in vacuo, the residue dissolved in an aprotic solvent such as methylene chloride, chloroform, benzene or the like, and washed with water, dried over sodium sulfate or magnesium sulfate and then concentrated in vacuo. After the reaction is performed in an aprotic solvent not miscible with water, the mixture is added into cold water, the organic layer separated, dried over sodium sulfate or magnesium sulfate, and then concentrated in vacuo. The residue is purified by direct crystallization or by chromatography on a silic gel G60 column using various solvent systems.

The silylated intermediates can be subsumed under general Formula III wherein:

X or X$^1$ is hydrogen.

The other is OR$^3$, a halogen such as fluorine, chlorine, bromine or iodine as well as a pseudohalogen such as the lower alkylsulfonyl group of 1 to 5 carbons such as methyl-, ethyl-, propyl-, isopropyl-, butyl-, isobutyl-, sec-butyl-, tert-butyl- and pentylsulfonyl or arylsulfonyl such as benzene-, p-toluene-, p-nitrobenzenesulfonyl grouping.

Among R$^1$, R$^2$ and R$^3$, one or two are trisubstituted-silyl groups such as tert-butyldimethyl-, tert-butyldiphenyl- or phenyldimethyl-silyl groupings, and the rest are hydrogen.

The intermediates of Formula III nucleosides are reacted with 1 or 2 equivalents of bromine under ultraviolet light irradiation in polyhalogenated carbon solvent such as carbon tetrachloride at a temperature range of from 0° to 77° C. in a period of from 1 to 6 hours. When 1 equivalent of bromine is used, 5-monobromomethyluracil nucleosides (Formula I, Y=CH$_2$Br) are formed. Reaction of Formula III intermediates with 2 equivalents of bromine results in the formation of 5-dibromomethyluracil nucleosides (Formula I, Y=CHBr$_2$).

Upon completion of the reaction, nitrogen gas is bubbled through th mixture for a period of from 10 minutes to 1 hour (preferably 30 minutes), to remove hydrogen bromide which is produced during the bromination reaction. The mixture is then concentrated in vacuo to afford crude bromomethyluracil intermediates (Formula I, Y=CH$_2$Br or CHBr$_2$) which can be purified as a very unstable powder. More practically, the mixture can be fluorinated directly without purification of the bromomethyluracil intermediates. Thus, the crude intermediates are dissolved in an appropriate, aprotic solvent and a fluorinating agent is added. When silver fluoride is used as a fluorinating agent, acetonitrile is the preferred solvent. When tetrabutylammonium fluoride is employed as the fluorinating agent tetrahydrofuran is the more suitable solvent. Acetone is recommended when Amberlyst A-26 (F$^-$) is used as the fluorinating agent.

The mixture is stirred vigorously at a temperature range of from −40° to 80° C. (preferably from −10° to 30° C.), for a period of from 5 minutes to 5 hours. The mixture is filtered from insoluble materials and the filtrate is washed with water, dried over sodium sulfate or magnesium sulfate, concentrated in vacuo, and the residue chromatographed over a column of silica gel G60 using various solvent systems, preferably n-hexane-ethyl acetate or a methylene chloride-tetrahydrofuran combination.

The free Formula I nucleosides wherein Y is CH$_2$F or CHF$_2$ and R$^1$ and R$^2$ are hydrogen, is prepared from the corresponding acyl intermediates (Formula III, wherein Y is CH$_2$F or CHF$_2$, R$^1$ and R$^2$ are the same and alkanoyl groups) by treatment with mineral acid in water or alkanol, preferably 1% to 5% hydrogen chloride in methanol. More preferably, the free nucleosides of Formula I are prepared from the corresponding partially silylated intermediates (Formula III, Y is CH$_2$F or CHF$_2$, R$^1$ and/or R$^2$ is/are trisubstituted silyl and X or X$^1$ is OH or trisubstituted silyloxy group) by treatment with fluoride ion in an appropriate solvent, preferably with tetra-n-butylammonium fluoride in tetrahydrofuran.

The free nucleosides (Formula I, Y is CH$_2$F or CHF$_2$, R$^1$ and R$^2$ are hydrogen) and their acylated analogs (Formula I, Y is CH$_2$F of CHF$_2$, R$^1$ and R$^2$ are the same or different alkanoyl) may be useful therapeutic agents exhibiting antiviral and/or anticancer activity, and may be employed in the form of pharmaceutical preparations which contain them in association with a compatible pharmaceutical carrier which can be an organic or inorganic inert carrier material suitable for enteral or parenteral administration such as, for example, water, gelatin, gum arabic, lactose, starches, magnesium stearate, talc, vegetable oils, polyalkylene glycols, petroleum jelly, etc. The pharmaceutical preparations can be made up in solid form (e.g., as tablets, dragees, suppositories or capsules), or in liquid form (e.g., as solutions, suspensions or emulsions). The preparations may be sterilized and/or may contain adjuvants such as preserving, stabilizing, wetting or emulsifying agents, salts for varying the osmotic pressure, or buffers. Such preparations may also contain other therapeutic agents.

The following examples are illustrative of the process and products of the present invention, but are not to be construed as limiting.

EXAMPLE 1

1-(2-Deoxy-2-fluoro-β-D-arabinofuranosyl)thymine (1.5 g, 5.76 mmol) is dissolved in dry pyridine (15 mL) and acetic anhydride (5 mL) is added. The mixture is stirred overnight at room temperature and is then concentrated in vacuo. The residue is chromatographed on a column of silica gel G60 using n-hexaneethyl acetate (1:2) as the eluent. Upon evaporation of the major UV-absorbing fraction, 1-(3,5-di-0-acetyl-2-deoxy-2-fluoro-β-D-arabinofuranosyl)thymine (1.62 g, 82%) is obtained as a colorless amorphous solid.

$^1$H NMR (CDCl$_3$) δ 1.94 (3H, s, Me), 2.13 (3H, s, Ac), 2.17 (3H, s, Ac), 4.25 (1H, m, H-4'), 4.44 (2H, m, H-5'5"), 5.10 (1H, dd, H-2', $J_{2',F}$=49.95. $J_{1',2'}$=2.74 Hz), 5.23 (1H, dd, H-3', $J_{3',F}$=16.88, $J_{2',3'}$=2.61), 6.22 (1H, dd, H-1', $J_{1',F}$=21.95, $J_{1',2'}$=2.74), 7.33 (1H, s, H-6), 9.91 (1H, s, NH, exchangeable).

Microanalysis (C$_{14}$H$_{17}$FN$_2$O$_7$). Calcd: C, 48.84; H, 4.98; N, 8.14. Found: C, 48.98; H, 5.12; N, 8.08.

By following the same procedure but using the corresponding 2'-substituted nucleosides as starting materials, the following compounds are also prepared:

1-(3',5'-Di-0-acetyl-2'-chloro-2'-deoxy-β-D-arabinofuranosyl)thymine;

1-(3',5'-Di-0-acetyl-2'-bromo-2'-deoxy-β-D-arabinofuranosyl)thymine;

1-(3',5'-Di-0-acetyl-2'-deoxy-2'-iodo-β-D-arabinofuranosyl)thymine;

1-(3',5'-Di-0-acetyl-2'-deoxy-2'-fluoro-β-D-ribofuranoysl)thymine;

1-(3',5'-Di-0-acetyl-2'-chloro-2'-deoxy-β-D-ribofuranosyl)thymine;

1-(3',5'-Di-0-acetyl-2'-bromo-2'-deoxy-β-D-ribofuranosyl)thymine; and 1-(3',5'-Di-0-acetyl-2'-deoxy-2'-iodo-β-D-ribofuranosyl)thymine.

EXAMPLE 2

A mixture of thymidine (0.50 g, 2.06 mmol) and tert-butyldiphenylsilyl chloride (0.60 mL) 2.31 mmol) in dry pyridine (10 mL) is stirred overnight at room temperature, and then concentrated in vacuo. The residue is dissolved in methylene chloride and the solution washed with water, dried over sodium sulfate and concentrated in vacuo. The residue is crystallized from acetone-n-hexane to afford 5'-0-tert-butyldiphenylsilyl-thymidine (600 mg), mp 170°-171° C. An additional amount (150 mg) of the silylated product is obtained from the mother liquor, giving a total yield of 76%. $^1$H NMR (CDCl$_3$) δ 1.09 (9H, s, t-Bu), 1.64 (3H, s, Me), 1.94–2.63 (2H, m, H-2',2"), 3.70–4.12 (3H, m, H-4',5',5"), 4.57 (1H, m, H-3'), 6.41 (1H, dd, H-1', $J_{1',2'}$=7.93, $J_{1',2''}$=6.10 Hz), 7.26–7.76 (11H, m, H-6 and Ph), 8.94 (1H, s, NH, exchangeable).

Microanalysis (C$_{26}$H$_{32}$N$_2$O$_5$Si). Calcd: C, 64.97; H, 6.71; N, 5.83. Found: C, 65.05; H, 6.75; N, 5.91.

By following the same procedure but using the corresponding 2'-substituted nucleoside analogs as starting materials, the following compounds are also prepared:

1-(5'-0-tert-Butyldiphenylsilyl-2-deoxy-2-fluoro-β-D-arabinofuranosyl)thymine;

1-(5'-0-tert-Butyldiphenylsilyl-2-chloro-2-deoxy-β-D-arabinofuranosyl)thymine;

1-(5'-0-tert-Butyldiphenylsilyl-2-bromo-2-deoxy-β-D-arabinofuranosyl)thymine;

1-(5'-0-tert-Butyldiphenylsilyl-2-deoxy-2-fluoro-β-D-ribofuranosyl)thymine;

1-(5'-0-tert-Butyldiphenylsilyl-2-chloro-2-deoxy-β-D-ribofuranosyl)thymine; and 1-(5'-0-tert-Butyldiphenylsilyl-2-bromo-2-deoxy-β-D-ribofuranosyl)thymine.

EXAMPLE 3

To a solution of 5-methyluridine (3.00 g., 10.06 mmol) and tert-butyldiphenylsilyl chloride (6.50 mL, 25.0 mmol) in dry N,N-dimethylformamide (60 mL) is added imidazole (3.00 g, 44.07 mmol), and the mixture is stirred overnight at room temperature. The solvent is removed in vacuo and the residue is partitioned between methylene chloride and water. The organic layer is separated, washed twice with water and concentrated in vacuo. The residue is chromatographed over a column of silica gel G60 using carbon tetrachloride-acetone (10:1) as the eluent. Two fractions are obtained. Upon evaporation of the first fraction in vacuo and crystallization of the residue from carbon tetrachloride-petroleum ether, 1-(2',5'-di-0-tert-butyldiphenyl-β-D-ribofuranosyl)thymine (3.78 g, 51%) is obtained, mp 97°-99° C. $^1$H NMR (CDCl$_3$) δ 0.92 (9H, s, t-Bu), 1.11 (9H, s, t-Bu), 1.58 (3H, d, 5-Me, $J_{Me,6}$=1.24 Hz), 3.73 (1H, dd, H-5', $J_{5',5''}$=11.73, $J_{4',5'}$=1.64), 3.91 (1H, dd, H-5", $J_{5',5''}$=11.73, $J_{4',5''}$=1.92), 4.18 (1H, m, H-4'), 4.39 (2H, m, H-2',3'), 6.20 (1H, m, H-1'), 6.78 (1H, d, H-6, $J_{Me,6}$=1.24), 7.10–7.71 (20H, m, Ph), 7.81 (1H, broad s, NH, exchangeable).

Microanalysis (C$_{42}$H$_{50}$N$_2$O$_6$Si$_2$.2H$_2$O) Calcd: C, 65.21; H, 7.06; N, 3.63. Found: C, 65.20; H, 7.10; N, 3.44.

From the second fraction, 1-(3',5'-di-0-tert-butyldiphenylsilyl-β-D-ribofuranosyl)thymine (1.86 g, 25%) is obtained, after rcrystalization from benzene-hexane, mp 86°-89° C. $^1$H NMR (CDCl$_3$) δ 0.96 (9H, s, t-Bu), 1.13 (9H, s, t-Bu), 1.49 (3H, s, 5-Me), 2.81 (1H, dd, H-5', $J_{5',5''}$=11.66, $J_{4',5'}$=1.92), 3.54 (1H, dd, H-5", $J_{5',5''}$=11.66, $J_{4',5''}$=1.38), 3.77 (1H, m, H-4'), 4.19 (1H, m, H-3'), 4.46 (1H, m, H-2'), 6.16 (1H, d, H-1', $J_{1',2'}$=7.68), 7.08–7.78 (21H, m, H-6 and Ph), 8.35 (1H, s, NH, exchangeable).

Microanalysis (C$_{42}$H$_{50}$N$_2$O$_6$Si$_2$) Calcd: C, 68.63; H, 6.80; N, 3.81. Found: C, 68.74; H, 7.09; N, 3.65.

By following the same procedure but using 1-(β-D-arabinofuranosyl)thymine as the starting material, 1-(3',5'-di-0-tert-butyldiphenylsilyl-β-D-arabinofuranosyl)thymine and 1-(2,5-di-0-tert-butyldiphenylsilyl-β-D-arabinofuranosyl)thymine are also prepared.

EXAMPLE 4

A mixture of 3',5'-di-0-acetylthymidine (4.50 g, 13.78 mmol) in carbon tetrachloride (900 ml) is refluxed under nitrogen until a clear solution is obtained. A solution of bromine (0.8 mL, 15.61 mmol) in carbon tetrachloride (18 mL) is very slowly added to the refluxing solution over a period of 2 to 3 hours, while the reaction mixture is irradiated with a 500 watt UV lamp. After all the bromine is added, nitrogen is bubbled through the solution for 30 minutes to remove hydrogen bromide. The solution is concentrated to dryness in vacuo. The crude 5-bromomethyluracil nucleoside intermediate thus obtained is dissolved in anhydrous acetonitrile (50 mL) and treated with powdered silver fluoride (8 g, 63.10 mmol) for 15 minutes with vigorous stirring at room temperature. The precipitate is removed by filtration and the filtrate is concentrated to dryness in vacuo. The residue is dissolved in chloroform, washed successively with water and saline, dried over sodium sulfate and concentraetd to dryness. The residue is chromatographed on a column of silica gel G60 using n-hexane-ethyl acetate (1:1). Upon evaporation of the major fraction in vacuo and crystallization of the residue from methylene chloride-ether-petroleum ether, 1-(3',5'-di-0-acetyl-β-D-erythropentofuranosyl)-5-monofluoromethyluracil (1.5 g, 32%) is obtained, mp 24°–27° C. $^1$H NMR (CDCl$_3$) δ 2.12 (6H, s, 3',5'-Ac), 2.24 (1H, m, H-2'), 2.57 (1H, dq, H-2", $J_{2',2''}$=14.27, $J_{1',2''}$=5.77, $J_{2'',3}$=2.06), 4.31 (3H, m, H-4',5',5''), 5.19 (2H, dd, CH$_2$F, $J_{H,F}$=47.48, $J_{H,H}$=3.29), 5.25 (1H, m, H-3'), 6.32 (1H, dd, H-1', $J_{1',2'}$=8.24, $J_{1',2''}$=5.77), 7.69 (1H, d, H-6, $J_{6,F}$=2.47).

Microanalysis (C$_{14}$H$_{17}$FN$_2$O$_7$) Calcd: C, 48.84; H, 4.98; F, 5.52; N, 8.14. Found: C, 49.14; H, 5.21; F, 5.21; N, 7.87.

EXAMPLE 5

1-(3',5'-Di-0-acetyl-2'-deoxy-2'-fluoro-β-D-arabinofuranosyl)thymine (170 mg, 0.49 mmol) is brominated by a procedure described in Example 4. The crude 5-bromomethyluracil nucleoside is dissolved in anhydrous tetrahydrofuran (1 mL) and 0.5M tetra-n-butylammonium fluoride in tetrahydrofuran (2 mL) is added. The mixture is stirred for 30 minutes at room temperature and then chromatographed on a silica gel G60 column using n-hexane-ethyl acetate (1:2) as the eluent. 1-(3,5-Di-0-acetyl-2-deoxy-2-fluoro-β-D-arabinofuranosyl)-5-monofluoromethyluracil (22 mg, 12%) is obtained after concentration of the nucleoside-containing fraction and crystallization of the residue from benzene; mp 109°–110° C. $^1$H NMR (CDCl$_3$) δ 2.12 (3H, s, Ac), 2.17 (3H, s, Ac), 4.26 (1H, m, H-4'), 4.46 (2H, m, H-5',5''), 5.13 (1H, dd, H-2', $J_{2',F}$=50.22, $J_{1',2'}$=2.74 Hz), 5.18 (2H, d, CH$_2$F, $J_{H,F}$=47.74), 5.24 (1H, dd, H-3', $J_{3',F}$=16.60, $J_{2',3'}$=2.06), 6.22 (1H, dd, H-1', $J_{1',F}$=21.40, $J_{1',2'}$=2.74), 7.73 (1H, broad s, H-6), 9.36 (1H, broad s, NH, exchangeable).

Microanalysis (C$_{14}$H$_{16}$F$_2$N$_2$O$_7$) Calcd: C, 46.41; H, 4.45; F, 10.49; N, 7.73. Found: C, 46.15; H, 4.51; F, 10.31; N, 7.75.

EXAMPLE 6

Crude 1-(5'-0-tert-butyldiphenylsilyl-2'-deoxy-β-D-erythropentofuranosyl)-5-monobromouracil (obtained by bromination of 5-0-tert-butyldiphenylsilylthymidine, (120 mg, 0.25 mmol) is dissolved in dry acetone (5 mL) and amberlyst A-26 (F$^-$) (0.5 g) is added. The mixture is vigorously stirred at room temperature for 1 hour and the resin is filtered and washed with acetone. The concentrated filtrate and washings are concentrated in vacuo and the residue chromatographed over a column of silica gel G60 using n-hexane-ethyl acetate (1:3). 1-(5'-0-tert-Butyldiphenylsilyl-2'-deoxy-β-D-erythopentofuranosyl)-5-monofluorouracil (26 mg, 21%) is obtained in pure form after crystallization from n-hexane-methylene chloride, mp 129°–131° C. $^1$H NMR (CDCl$_3$) δ 1.04 (3H, s, Me in tBu), 1.08 (6H, s, 2Me in tBU), 1.96–2.62 (2H, m, H-2',2''), 3.75–4.19 (3H, m, H-4',5',5''), 4.80 (2H, d, CH$_2$F, $J_{H,F}$=47.92 Hz), 6.22 (1H, dd, H-1', $J_{1',2'}$=5.76, $J_{1',2'''}$=7.41), 7.29–7.77 (10H, m, Ph), 7.83 (1H, d, H-6, $J_{6,F}$=3.35), 8.45 (1H, broad s, NH, exchangeable).

Microanalysis (C$_{26}$H$_{21}$FN$_2$O$_5$Si) Calcd: C, 62.63; H, 6.27; F, 3.81; N, 5.62. Found: C, 62.66; H, 6.36; F, 3.66; N, 5.78.

The following 5-monofluoromethyluracil nucleosides are prepared by following the same procedures described in Example 4 and Example 6 but using the corresponding blocked nucleoside intermediates. When the silver fluoride-acetone combination as in Example 4 is used, the yields are 30%–55%, whereas the Amberlyst A-26 (F$^-$)-acetone procedure as in Example 6 gives the following products in 20%–40% yields:

1-(3',5'-Di-0-acetyl-2'-deoxy-2'-fluoro-β-D-arabinofuranosyl)-5-monofluoromethyluracil;
1-(3',5'-Di-0-acetyl-2'-chloro-2'-deoxy-β-D-arabinofuranosyl)-5-monofluoromethyluracil;
1-(3',5'-Di-0-acetyl-2'-bromo-2'-deoxy-β-D-arabinofuranosyl)-5-monofluoromethyluracil;
1-(5'-0-tert-Butyldiphenylsilyl-2'-deoxy-2'-fluoro-β-D-arabinofuranosyl)-5-monofluoromethyluracil;
1-(5'-0-tert-Butyldiphenylsilyl-2'-chloro-2'-deoxy-β-D-arabinofuranosyl)-5-monofluoromethyluracil;
1-(5'-0-tert-Butyldiphenylsilyl-2'-bromo-2'-deoxy-β-D-arabinofuranosyl)-5-monofluoromethyluracil;
1-(2',3',5'-Tri-0-acetyl-β-D-arabinofuranosyl)-5-monofluoromethyluracil;
1-(2',5'-Di-0-tert-butyldiphenylsilyl-β-D-arabinofuranosyl)-5-monofluoromethyluracil;
1-(3',5'-Di-0-tert-butyldiphenylsilyl-β-D-arabinofuranosyl)monofluoromethyluracil;
3',5'-Di-0-acetyl-2'-deoxy-2'-fluoro-5-monofluoromethyluridine;
3',5'-Di-0-acetyl-2'-chloro-2'-deoxy-5-monofluoromethyluridine;
3',5'-Di-0-acetyl-2'-bromo-2'-deoxy-5-monofluoromethyluridine;
5'-0-tert-Butyldiphenylsilyl-2'-deoxy-2'-fluoro-5-monofluoromethyluridine;
5'-0-tert-Butyldiphenylsilyl-2'-chloro-2'-deoxy-5-monofluoromethyluridine;
5'-0-tert-Butyldiphenylsilyl-2'-bromo-2'-deoxy-5-monofluoromethyluridine;
2',3',5'-Tri-0-acetyl-5-monofluormethyluridine;
2',5'-Di-0-tert-butyldiphenylsilyl-5-monofluoromethyluridine; and
3',5'-Di-0-tert-butyldiphenylsilyl-5-monofluoromethyluridine.

By following the procedure of Example 5 but using the corresponding acetylated nucleosides as the intermediates, the following nucleosides are also prepared in 10%–20% yield:

1-(3',5'-Di-0-acetyl-2'-chloro-2'-deoxy-β-D-arabinofuranosyl)-5-monofluoromethyluracil;
1-(3',5'-Di-0-acetyl-2'-bromo-2'-deoxy-β-D-arabinofuranosyl)-5-monofluoromethyluracil;
1-(2',3',5'-Tri-0-acetyl-β-D-arabinofuranosyl)-5-monofluoromethyluracil;
3',5'-Di-0-acetyl-2'-deoxy-5-monofluoromethyluridine;
3',5'-Di-0-acetyl-2'-deoxy-2'-fluoro-5-monofluoromethyluridine;
3',5'-Di-0-acetyl-2'-chloro-2'-deoxy-5-monofluoromethyluridine;
3',5'-Di-0-acetyl-2'-bromo-2'-deoxy-5-monofluoromethyluridine; and
2',3',5'-Tri-0-acetyl-5-monofluoromethyluridine.

EXAMPLE 7

A solution of bromine (0.118 mL, 2.30 mmol) in carbon tetrachloride (2 mL) is slowly blown with a stream of dry nitrogen into a refluxing solution of 1-(5'-0-tert-butyldiphenylsilyl-2'-deoxy-2'-fluoro-β-D-arabinofuranosyl)thymine (498 mg, 1 mmol) in carbon tetrachloride while irradiated with a UV light. After 30 minutes, when all the bromine is added, nitrogen is bubbled through the solution for a further 15 minutes to remove the hydrogen bromide.

The solution is concentrated to dryness in vacuo and the residue dissolved in dry acetonitrile (100 mL). Finely pulverized silver fluoride (1.0 g, 7.88 mmol) is added to the solution and the mixture is stirred vigorously for 15 minutes at room temperature. The mixture is filtered and the filtrate is concentrated in vacuo. The residue is dissolved in chloroform, washed with water and saline, dried over sodium sulfate and concentrated in vacuo. The residue is chromatographed on a column of silica gel G60 using methylene chloride-tetrahydrofuran (20:1 to 10:1) as the eluent. The UV absorbing fraction eluted with 10:1 methylene chloride-tetrahydrofuran is concentrated and the residue crystallized from methylene chloride-petroleum ether. 1-(5'-O-tert-Butyldiphenylsilyl-2'-deoxy-2'-fluoro-$\beta$-D-arabinofuranosyl)-5-difluoromethyluracil (80 mg, 15%) is obtained, mp 132°-134° C. $^1$H NMR (CDCl$_3$) $\delta$ 1.08 (9H, s, tBu), 3.75–4.09 (3H, m, H-4',5',5''), 4.55 (1H, dq, H-3', $J_{3',F}$=22.23, $J_{2',3'}$=0.82, $J_{3',4'}$=0 Hz), 5.05 (1H, dq, H-2', $J_{2',F}$=51.05, $J_{1',2'}$=3.30, $J_{2',3'}$=0.82), 6.77 (1H, dd, H-1', $J_{1',F}$=19.49, $J_{1',2'}$=3.30), 6.56 (1H, t, CHF$_2$, $J_{H,F}$=54.75), 7.23–7.81 (10H, m, Ph), 7.87 (1H, d, H-6, $J_{6,F}$=1.37), 8.79 (1H, broad s, NH, exchangeable).

Microanalysis (C$_{26}$H$_{29}$F$_3$N$_2$O$_5$Si) Calcd: C, 58.41; H, 5.47; F, 10.66; N, 5.24. Found: C, 58.58; H, 5.69; F, 10.49; N, 5.19.

By following the same procedure but using the corresponding protected nucleosides, the following 5-difluoromethyluracil nucleosides are prepared:

1-(3',5'-Di-0-acetyl-2'-deoxy-$\beta$-D-erythropentofuranosyl)-5-difluoromethyluracil;
1-(2',5'-Di-0-acetyl-2'-deoxy-2'-fluoro-$\beta$-D-arabinofuranosyl)-5-difluoromethyluracil;
1-(3',5'-Di-0-acetyl-2'-chloro-2'-deoxy-$\beta$-D-arabinofuranosyl)-5-difluoromethyluracil;
1-(3',5'-Di-0-acetyl-2'-bromo-2'-deoxy-$\beta$-D-arabinofuranosyl)-5-difluoromethyluracil;
1-(2',3',5'-Tri-0-acetyl-$\beta$-D-arabinofuranosyl)-5-difluoromethyluracil;
1-(5'-0-tert-Butyldiphenylsilyl-2'-chloro-2'-deoxy-$\beta$-D-arabinofuranosyl)-5-difluoromethyluracil;
1-(5'-0-tert-Butyldiphenylsilyl-2'-bromo-2'-deoxy-$\beta$-D-arabinofuranosyl)-5-difluoromethyluracil;
1-(2',5'-Di-0-tert-butyldiphenylsilyl-$\beta$-D-arabinofuranosyl)-5-difluoromethyluracil;
1-(3',5'-Di-0-tert-butyldiphenylsilyl-$\beta$-D-arabinofuranosyl)-5-difluoromethyluracil;
3',5'-Di-0-acetyl-2'-deoxy-2'-fluoro-5-difluoromethyluridine;
3',5'-Di-0-acetyl-2'-chloro-2'-deoxy-5-difluoromethyluridine;
3',5'-Di-0-acetyl-2'-bromo-2'-deoxy-5-difluoromethyluridine;
2',3',5'-Tri-0-acetyl-5-difluoromethyluridine;
5'-0-tert-Butyldiphenylsilyl-2'-deoxy-2'-fluoro-5-difluoromethyluridine;
5'-0-tert-Butyldiphenylsilyl-2'-chloro-2'-deoxy-5-difluoromethyluridine;
5'-0-tert-Butyldiphenylsilyl-2'-bromo-2'-deoxy-5-difluoromethyluridine;
2',5'-Di-0-tert-butyldiphenylsilyl-5-difluoromethyluridine; and
3',5'-Di-0-tert-butyldiphenylsilyl-5-difluoromethyluridine.

EXAMPLE 8

1-(5'-0-tert-Butyldiphenylsilyl-2'-deoxy-$\beta$-D-erythropentofuranosyl)-5-monofluoromethyluracil (440 ml, 0.88 mmol) is dissolved in dry tetrahydrofuran (4 mL) and 0.5M tetra-n-butylammonium fluoride in tetrahydrofuran (2.2 mL) is added. The mixture is stirred at room temperature for 90 minutes and then concentrated in vacuo. The residue is chromatographed on a silica gel G60 column using methylene chloride-tetrahydrofuran (1:1) as the eluent. After concentration of the UV absorbing fraction, the residue is crystallized from acetone to give 2'-deoxy-5-monofluoromethyluridine, 143 mg (63%), mp 140° C. (dec). $^1$H NMR (d$_6$-acetone) $\delta$ 2.21 (2H, m, H-2',2''), 3.71 (2H, m, H-5',5''), 3.88 (1H, apparent dd, H-4', $J_{3',4'}$=3.16, $J_{4',5'}$=6.17, $J_{4',5''}$=0 Hz), 4.39 (1H, m, H-3'), 4.96 (2H, d, CH$_2$F, $J_{H,F}$=49.12), 6.20 (1H, apparent t, H-1', $J_{1',2'}$=$J_{1',2''}$=6.59), 8.23 (1H, d, H-6, $J_{6,F}$=4.12).

Microanalysis(C$_{10}$H$_{13}$FN$_2$O$_5$) Calcd: C, 46.16; H, 5.03; F, 7.30; N, 10.76. Found: C, 46.28; H, 5.31; F, 7.16; N, 10.58.

By following the same procedure but using the corresponding silylated nucleoside intermediates, the following 5-(partially fluorinated)methyluracil nucleosides are prepared:

1-(2'-Deoxy-2'-fluoro-$\beta$-D-arabinofuranosyl)-5-monofluoromethyluracil;
1-(2'-chloro-2'-deoxy-$\beta$-D-arabinofuranosyl)-5-monofluoromethyluracil;
1-(2'-Bromo-2'-deoxy-$\beta$-D-arabinofuranosyl)-5-monofluoromethyluracil;
1-($\beta$-D-arabinofuranosyl)-5-monofluoromethyluracil;
2'-Deoxy-2'-fluoro-5-monofluoromethyluridine;
2'-Chloro-2'-deoxy-5monofluoromethyluridine;
2'-Bromo-2'-deoxy-5-monofluoromethyluridine;
5-Monofluoromethyluridine;
1-(2'-Deoxy-2'-fluoro-$\beta$-D-arabinofuranosyl)-5-difluoromethyluracil;
1-(2'-Chloro-2'-deoxy-$\beta$-D-arabinofuranosyl)-5-difluoromethyluracil;
1-(2'-Bromo-2'-deoxy-$\beta$-D-arabinofuranosyl)-5-difluoromethyluracil;
1-($\beta$-D-Arabinofuranosyl)-5-difluorouracil;
2'-Deoxy-5-difluoromethyluridine;
5-Difluoromethyluridine;
2'-Deoxy-2'-fluoro-5-difluoromethyluridine;
2'-Chloro-2'-deoxy-5-difluoromethyluridine; and
2'-Bromo-2'-deoxy-5-difluoromethyluridine.

The results of antiviral assay of some representative nucleosides are given in Table 1.

TABLE 1

Antiherpes Activity of α-fluorinated thymine nucleosides.

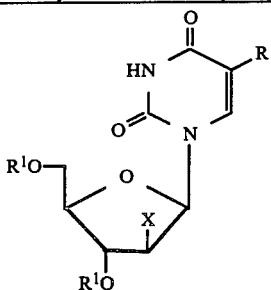

| | R | R¹ | X | Inhibitory Concentration (μM) HSV-1 | HSV-2 | Toxic Concentration (μM) |
|---|---|---|---|---|---|---|
| | CH₂F | H | H | >100 | >100 | 1,000 |
| | CH₂F | Ac | H | >100 | >100 | 1,000 |
| | CHF₂ | H | H | 1.40 | 1.66 | 1,000 |
| | CHF₂ | Ac | H | 17.0 | 25.1 | 1,000 |
| | CH₂F | H | F | 0.21 | 0.18 | 1,000 |
| | CH₂F | Ac | F | 2.46 | 5.19 | 1,000 |
| | CHF₂ | H | F | 0.48 | 1.04 | 1,000 |
| | CHF₂ | Ac | F | 0.71 | 2.16 | 1,000 |
| (FMAU) | CH₃ | H | F | 0.10 | 0.05 | 1,000 |
| | CH₃ | Ac | F | 0.44 | 1.23 | 1,000 |

Each of the nucleosides was initially dissolved in a diluent containing 60% propylene glycol and 10% EtOH; subsequent dilutions used maintenance culture medium. Agents were assessed at tenfold dilutions with final concentrations ranging from 10,000 to 0.01 micromolar.

Confluent human foreskin monolayers were maintained in 96-well microtiter plates using Eagle's Minimal Essential Medium supplemented with 2% fetal bovine serum, antibiotics and glutamine using standard methods.[40] Prior to virus inoculation, the medium was removed from each well and replaced with 100 μL of agent diluted in maintenance medium with differing concentrations in each horizontal row, beginning with the highest concentration in the upper row, with subsequent tenfold dilutions in the next rows and the last (control) row fed with agent-free maintenance medium. The virus inocula were then added, suspended in 100 μL of maintenace medium. A high-dose inoculum which induced nearly confluent (100%) cytopathic effect (CPE) two days later was added to the first five vertical columns of the plate (1-5) and, similarly, a low-dose inoculum inducing approximately 50% CPE in each well two days later was added to the next five vertical columns (6-10). To the last two columns, virus-free medium was added to serve as uninfected control wells in order to assess direct cellular cytotoxicity at each agent dilution. The plates were then incubated at 36.5° C. in 5% CO₂ in air for two days, at which time they were read.

The cytopathology of each well was read using an inverted microscope and scored from 0 to 4 (0=no CPE and 4=>95% CPE); for marginal or equivocal readings a + or − is affixed to each score. For calculation of the inhibitory concentrations (IC) of agents and interpolating between dilutions of agents, each well reading was converted to a numerical score (4=40, 4−=37, 3+=33, 3=30, etc). The mean score of each five wells in a row receiving a given agent dilution and virus inoculum was then calculated and compared with an appropriate control row receiving no agent. Significant inhibition was judged to occur when the mean well score at a given agent concentration was lower than the mean value of the control row by 10 scoring units. When the value fell between two rows, simple arithmetic interpolation was done to calculate the agent concentrate at the point on a slope between the mean scores in the rows above and below this point. The IC values of each agent using the high and low virus inocula were then averaged yielding a final mean IC which was expressed as a micromolar drug concentration.

Although α,α,α-trifluorothymidine (Formula IV, R=CF₃, X=H, R¹=H) is reported to be antiherpetic and very cytotoxic, the α,α-difluoro analog (Formula IV, R=CHF₂, X=H or Ac, R¹=H) showed very potent antiherpes activity without serious cytotoxicity. In the FMAU series, fluorination of the 5-methyl group does not alter the antiherpetic activity significantly.

The acetylated derivatives may act as masked precursors which may be saponified by esterases to release active free nucleosides. The ¹⁸F-labeled nucleosides which can be prepared by the methods we developed may be useful for diagnosis of herpes encephalitis, employing Positron Emission Tomography scanning.

What is claimed is:

1. Pyrimidine nucleosides having the formula:

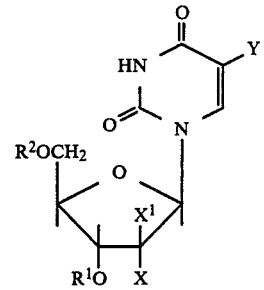

wherein
either X or X' is H and the other is a halogen, a substituted sulfonyl group or OR³, wherein R³ is H, an organic acyl or a trisubstituted-silyl group;
Y is CH₂F or CHF₂; and
R¹ and R² are the same or different and are H, an organic acyl or a trisubstituted-silyl group.

2. Nucleosides selected from the group of:
1-(3',5'-Di-O-acetyl-2'-deoxy-2'-fluoro-β-D-arabinofuranosyl)thymine,
1-(3',5'-Di-O-acetyl-2'-deoxy-2'-iodo-β-D-arabinofuranosyl)thymine,
1-(3',5'-Di-O-acetyl-2'-deoxy-2'-fluoro-β-D-ribofuranosyl)thymine,
1-(3',5'-Di-O-acetyl-2'-chloro-2'-deoxy-β-D-ribofuranosyl)thymine,
1-(3',5'-Di-O-acetyl-2'-bromo-2'-deoxy-β-D-ribofuranosyl)thymine, and
1-(3',5'-Di-O-acetyl-2'-deoxy-2'-iodo-β-D-ribofuranosyl)thymine.

3. Nucleosides selected from the group consisting of:
5'-O-tert-Butyldiphenylsilylthymidine,
1-(5'-O-tert-Butyldiphenylsilyl-2'-deoxy-2'-fluoro-β-D-arabinofuranosyl)thymine,
1-(5'-O-tert-Butyldiphenylsilyl-2'-chloro-2'-deoxy-β-D-arabinofuranosyl)thymine,
1-(5'-O-tert-Butyldiphenylsilyl-2'-bromo-2'-deoxy-β-D-arabinofuranosyl)thymine,
1-(2',5'-Di-O-tert-butyldiphenylsilyl-β-D-arabinofuranosyl)thymine, 1-(3',5'-Di-O-tert-butyldiphenylsilyl-β-D-arabinofuranosyl)thymine,
1-(5'-O-tert-Butyldiphenylsilyl-2'-deoxy-2'-fluoro-β-D-ribofuranosyl)thymine,
1-(5'-O-tert-Butyldiphenylsilyl-2'-chloro-2'-deoxy-β-D-ribofuranosyl)thymine,
1-(5'-O-tert-Butyldiphenylsilyl-2'-bromo-2'-deoxy-β-D-ribofuranosyl)thymine,
1-(2',5'-Di-O-tert-butyldiphenylsilyl-β-D-ribofuranosyl)thymine, and
1-(3',5'-Di-O-tert-butyldiphenylsilyl-β-D-ribofuranosyl)thymine.

4. Nucleosides of claim 1 selected from the group consisting of:
1-(3',5'-Di-O-acetyl-2'-deoxy-2'-fluoro-β-D-arabinofuranosyl)-5-monofluoromethyluracil,
1-(3',5'-Di-O-acetyl-2'-chloro-2'-deoxy-β-D-arabinofuranosyl)-5-monofluoromethyluracil,
1-(3',5'-Di-O-acetyl-2'-bromo-2'-deoxy-β-D-arabinofuranosyl)-5-monofluoromethyluracil,
1-(2',3',5'-Tri-O-acetyl-β-D-arabinofuranosyl)-5-monofluoromethyluracil,
3',5'-Di-O-acetyl-2'-deoxy-5-monofluoromethyluridine,
3',5'-Di-O-acetyl-2'-deoxy-2'-fluoro-5-monofluoromethyluridine,
3',5'-Di-O-acetyl-2'-chloro-2'-deoxy-5-monofluoromethyluridine,
3',5'-Di-O-acetyl-2'-bromo-2'-deoxy-5-monofluoromethyluridine, and
2',3',5'-Tri-O-acetyl-5-monofluoromethyluridine.

5. Nucleosides of claim 1 selected from the group consisting of:
1-(5'-O-tert-Butyldiphenylsilyl-2'-deoxy-2'-fluoro-β-D-arabinofuranosyl)-5-monofluoromethyluracil,
1-(5'-O-tert-Butyldiphenylsilyl-2'-chloro-2'-deoxy-β-D-arabinofuranosyl)-5-monofluoromethyluracil,
1-(5'-O-tert-Butyldiphenylsilyl-2'-bromo-2'-deoxy-β-D-arabinofuranosyl)-5-monofluoromethyluracil,
1-(2',5'-Di-O-tert-butyldiphenylsilyl-β-D-arabinofuranosyl)-5-monofluoromethyluracil,
1-(3',5'-Di-O-tert-butyldiphenylsilyl-β-D-arabinofuranosyl)-5-monofluoromethyluracil,
5'-O-tert-Butyldiphenylsilyl-2'-deoxy-5-monofluoromethyluridine,
5'-O-tert-Butyldiphenylsilyl-2'-deoxy-2'-fluoro-5-monofluoromethyluridine,
5'-O-tert-Butyldiphenylsilyl-2'-chloro-2'-deoxy-5-monofluoromethyluridine,
5'-O-tert-Butyldiphenylsilyl-2'-bromo-2'-deoxy-5-monofluoromethyluridine,
2',5'-Di-O-tert-butyldiphenylsilyl-5-monofluoromethyluridine, and
3',5'-Di-O-tert-butyldiphenylsilyl-5-monofluoromethyluridine.

6. Nucleosides of claim 1 selected from the group consisting of:
1-(3',5'-Di-O-acetyl-2'-deoxy-2'-fluoro-β-D-arabinofuranosyl)-5-difluoromethyluracil,
1-(3',5'-Di-O-acetyl-2'-chloro-2'-deoxy-β-D-arabinofuranosyl)-5-difluoromethyluracil,
1-(3',5'-Di-O-acetyl-2'-bromo-2'-deoxy-β-D-arabinofuranosyl)-5-difluoromethyluracil,
1-(2',3',5'-Tri-O-acetyl-β-D-arabinofuranosyl)-5-difluoromethyluracil,
3',5'-Di-O-acetyl-2'-deoxy-5-difluoromethyluridine,
3',5'-Di-O-acetyl-2'-deoxy-2'-fluoro-5-difluoromethyluridine,
3',5'-Di-O-acetyl-2'-chloro-2'-deoxy-5-difluoromethyluridine,
3',5'-Di-O-acetyl-2'-bromo-2'-deoxy-5-difluoromethyluridine, and
2',3',5'-Tri-O-acetyl-5-difluoromethyluridine.

7. Nucleosides of claim 1 selected from the group consisting of:
1-(5'-O-tert-Butyldiphenylsilyl-2'-deoxy-2'-fluoro-β-D-arabinofuranosyl)-5-difluoromethyluracil,
1-(5'-O-tert-Butyldiphenylsilyl-2'-chloro-2'-deoxy-β-D-arabinofuranosyl)-5-difluoromethyluracil,
1-(5'-O-tert-Butyldiphenylsilyl-2'-bromo-2'-deoxy-β-D-arabinofuranosyl)-5-difluoromethyluracil,
1-(2',5'-Di-O-tert-butyldiphenylsilyl-β-D-arabinofuranosyl)-5-difluoromethyluracil,
1-(3',5'-Di-O-tert-butyldiphenylsilyl-β-D-arabinofuranosyl)-5-difluoromethyluracil,
5'-O-tert-Butyldiphenylsilyl-2'-deoxy-5-difluoromethyluridine,
5'-O-tert-Butyldiphenylsilyl-2'-deoxy-2'-fluoro-5-difluoromethyluridine,
5'-O-tert-Butyldiphenylsilyl-2'-deoxy-2'-fluoro-5-difluoromethyluridine,
5'-O-tert-Butyldiphenylsilyl-2'-chloro-2'-deoxy-5-difluoromethyluridine,
5'-O-tert-Butyldiphenylsilyl-2'-bromo-2'-deoxy-5-difluoromethyluridine,
2',5'-Di-O-tert-butyldiphenylsilyl-5-difluoromethyluridine, and
3',5'-Di-O-tert-butyldiphenylsilyl-5-difluoromethyluridine.

8. Nucleosides of claim 1 selected from the group consisting of:
1-(2'-Deoxy-2'-fluoro-β-D-arabinofuranosyl)-5-monofluoromethyluracil,
1-(2'-Chloro-2'-deoxy-β-D-arabinofuranosyl)-5-monofluoromethyluracil,
1-(2'-Bromo-2'-deoxy-β-D-arabinofuranosyl)-5-monofluoromethyluracil,
1-(β-D-Arabinofuranosyl)-5-monofluoromethyluridine,
5-Monofluoromethyluridine,
2'-Deoxy-5-monofluoromethyluridine,
2'-Deoxy-2'-fluoro-5-monofluoromethyluridine,
2'-Deoxy-2'-chloro-5-monofluoromethyluridine, and
2'-Deoxy-2'-bromo-5-monofluoromethyluridine.

9. Nucleosides of claim 1 selected from the group consisting of:
1-(2'-Deoxy-2'-fluoro-β-D-arabinofuranosyl)-5-difluoromethyluracil,
1-(2'-Chloro-2'-deoxy-β-D-arabinofuranosyl)-5-difluoromethyluracil,
1-(2'-Bromo-2'-deoxy-β-D-arabinofuranosyl)-5-difluoromethyluracil,
1-(β-D-Arabinofuranosyl)-5-difluoromethyluracil,
5-Difluoromethyluridine,
2'-Deoxy-5-difluoromethyluridine,
2'-Deoxy-2'-fluoro-5-difluoromethyluridine,
2'-Chloro-2'-deoxy-5-difluoromethyluridine, and
2'-Bromo-2'-deoxy-5-difluoromethyluridine.

10. Pharmaceutical composition useful as an antiviral agent comprising an effective amount of nucleoside of claim 1 and a pharmaceutically acceptable carrier.

* * * * *